United States Patent [19]

Van Veen

[11] Plant 4,241

[45] Apr. 18, 1978

[54] ROSE PLANT

[75] Inventor: Jan Van Veen, Aalsmeer, Netherlands

[73] Assignee: Carlton Rose Nurseries, Inc., Carlton, Oreg.

[21] Appl. No.: 784,782

[22] Filed: Apr. 5, 1977

[51] Int. Cl.[2] ..... A01H 5/00

[52] U.S. Cl. ..... Plt./18

[58] Field of Search ..... Plt./18

*Primary Examiner*—Robert E. Bagwill

*Assistant Examiner*—James R. Feyrer

*Attorney, Agent, or Firm*—Burns, Doane, Swecker & Mathis

[57] ABSTRACT

A rose plant of the Hybrid Tea Class obtained as a seedling from a seed parent of the White Satin variety U.S. Plant Pat. No. 2,648) and unnamed pollen parent U.S. Plant Pat. No. 2,603. The rose plant of the new and distinct variety freely yields long lasting large blooms borne on long stems on a continuous basis in a greenhouse.

14 Drawing Figures

SUMMARY OF THE INVENTION

The object of the present invention is to provide a hardy rose plant of the Hybrid Tea Class which is capable of freely yielding quality cut flowers under greenhouse conditions.

The variety of rose plant of the present invention was obtained at Aalsmeer, Holland, as a seedling from a seed parent of the White Satin variety (U.S. Plant Pat. No. 2,648) and unnamed pollen parent U.S. Plant Pat. No. 2,603. The crossing was made during 1972, the sowing during 1973, and the first flower appeared during 1973. The new variety was initially designated Rose U.S. Plant Pat. No. 3,667.

Asexual reproduction of my new and distinct variety shows that its unique combination of characteristics come true to form and are established and transmitted through succeeding propagations.

BRIEF DESCRIPTION OF THE DRAWINGS

The accompanying photographs show typical specimens of the vegetative growth and flowers of the new variety in different stages of development and are depicted in color as nearly true as it is reasonably possible to make the same in color illustrations of this character.

FIG. 2 is a developing bud;

FIG. 3 shows a flower when starting to open;

FIG. 4 shows a nearly open flower;

FIG. 5 shows a cross-section of a fully open flower with the stamens, pistils, and receptacle showing;

FIG. 6 shows a receptacle with the stamens removed and pistils showing;

FIG. 7 shows an outer petal, top-inside surface, bottom-outer surface;

FIG. 8 shows an intermediate petal, top-inside surface, bottom-outer surface;

FIG. 9 shows an inner petal, top-inside surface, bottom-outer surface;

FIG. 10 shows one of the leaves with a composition of three leaflets showing the upper surface;

FIG. 11 shows one of the leaves with a composition of five leaflets showing the upper surface;

FIG. 12 shows a leaf with a composition of five leaflets showing the under surface;

FIG. 13 shows a stem with branches; and

FIG. 14 shows a new growth with a developing bud and leaf.

DETAILED DESCRIPTION OF THE DISCLOSURE

Figure 1:
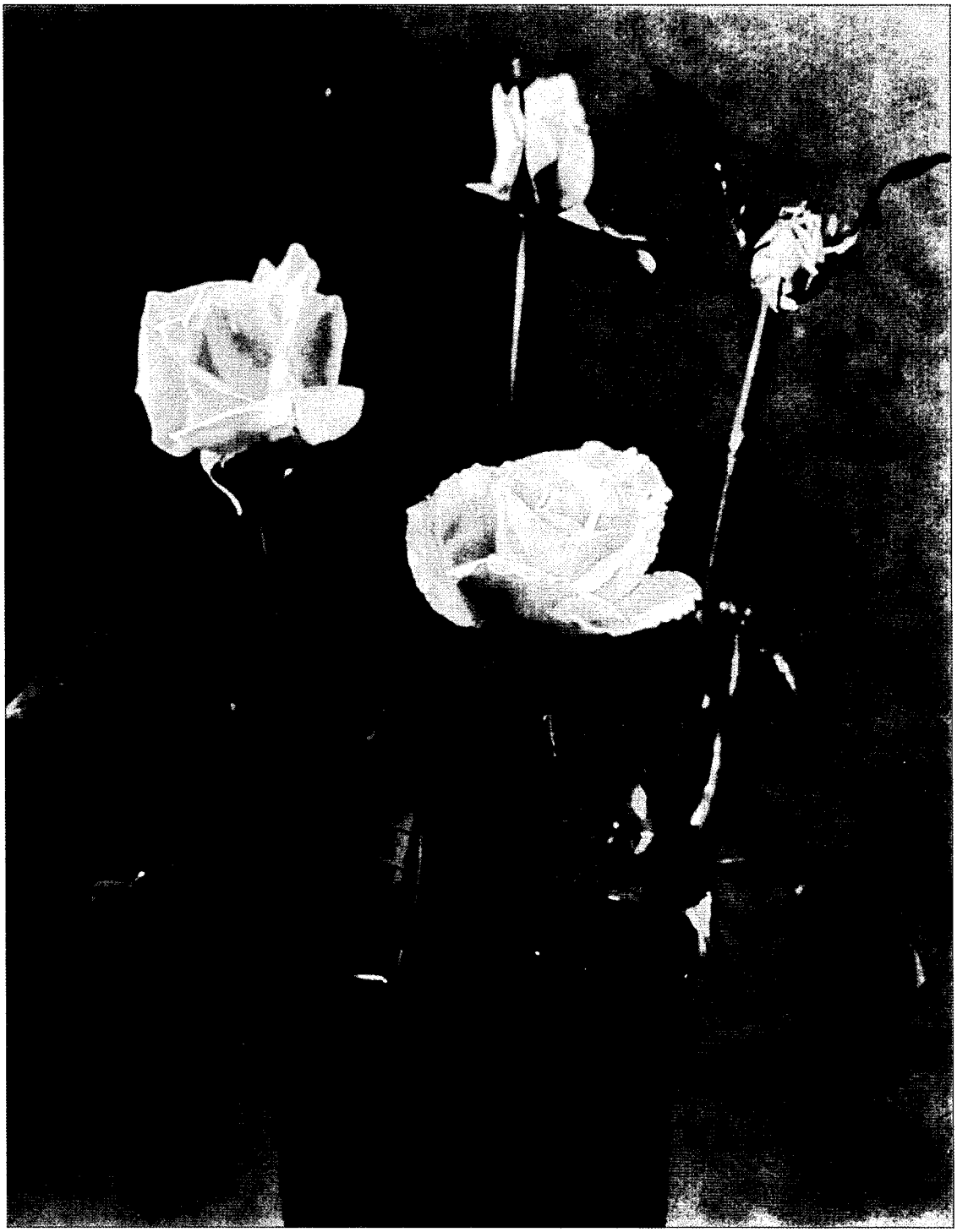
FIG. 1 is a view of several flowers in different stages of development.

The following description was made during October, 1976 of the rose plants of the new and distinct variety growing in a greenhouse at Salinas, Calif. Color designations are to *A Dictionary of Color* by A. Maerz and M. Rea Paul, McGraw-Hill Book Co. (New York and London — 1930).

FLOWER

Flowers borne: Singly to stems of long length having normal strength.

Quantity of bloom: Free in greenhouse.

Continuity: Continuous.

Fragrance: Moderate; sweetbriar.

Bud:

*Peduncle.*—Long, medium-heavy; erect; light green; almost smooth.

*Before calyx breaks.*—Size: medium. Form: ovoid with a conspicuous neck; with foliaceous appendages on the surface of the bud; with cut foliaceous parts extending beyond the tip of the bud equal to $\frac{3}{4}$ or more of its length.

*As calyx breaks.*—Color: Plate I, B4, Arbutus.

*As first petal opens.*—Color: Outside: Plate I, F/4, France Rose. Inside: Plate II, J/3, Rose Nilsson. Opening: It does open up well.

Bloom:

*Size when fully open.*—Large: 4 inches to $4\frac{1}{2}$ inches.

*Petalage.*—Very double.

*Form.*—Full high centered globular at first; becoming flat high centered; petals remaining at first loosely rolled outward; becoming later at maturity very loosely rolled outward.

Petals: Medium thick; with inside satiny; outside velvety.

*Shape.*—Outer: ovate; with 1 notch. Intermediate: ovate, undulate; apex flat; with 1 tooth. Inner: round; ovate; undulate; tapered apex; with 1 notch.

*Color.*—Colors may be modified by being shaded with other colors. Color of newly opened flower: Outer petal: Outside surface: Plate 49, B/1, Pale pink base, shading to a darker pink toward middle and outer one fourth, Plate 50, D/4. Inside surface: Plate 50, D/3, Near Cameo Pink, finely lined or veined with darker pink, Plate 50, E/5, creamy-yellow near the base. Intermediate petal: Outside surface: Plate 51, H/1, Persian Lilac, lighter near the base, Plate 51, B/1. Inside surface: Plate 51, H/1, Persian Lilac. Inner petal: Outside surface: Plate 50, I/1, Thulite Pink shading to a creamy base with yellow tooth. Inside surface: Plate 50, I/1, Thulite Pink shading to creamy pink near base. Color of flower 3 days after opening: Outer petal: Outside surface: Plate 49, C/1 to middle shading to Plate 49, B/1 at the base. Inside surface: Plate 51, H/1, Persian Lilac shading to Plate 51, A/1 to an Ivory White at the base. Inner petal: Outside surface: Plate 50, C/2, Cameo Pink. Inside surface: Plate 50, F/1, near Thulite Pink. General color effect: Newly opened flower: Soft Cameo Pink. Three days open: Plate 50, I/1, Thulite Pink.

*Behavior.*—Drop off cleanly.

*Flower longevity.*—Cut roses grown in greenhouse kept at living room temperature 7 days during October.

REPRODUCTIVE ORGANS

Stamens: Many; arranged irregularly about pistils.
Filaments: Many; with anthers, medium length.
*Color.*—Plate 9, K/4, Jasmine.
Anthers: Open at various times; medium size.
*Color.*—Plate 9, J/7, Deep Chrome. Seldom fused with a petaloid.
Pollen: Abundant; yellow-gold.
Pistils: Many.
Styles: Short-medium length, thin; bunched.
Stigma: Yellow with white base.
Ovaries: Some protruding from receptacle.
Hips: Medium; globular with inconspicuous pear-shaped neck; very smooth; thick fleshy walls; green.
Sepals: Falling soon; spear-shaped; recurved.
Seeds: Few; large.

PLANT

Foliage:
*Leaves.*—Compound of 3 and 5; normal quantity; medium size; moderately leathery; glossy.
*Leaflet.*—Shape: ovoid; apex acute; base margin serrate. Color: Mature upper surface: Plate 24, L/1, Yew Green. Mature under surface: Plate 22, I/5, Sage Green. Young upper surface: Plate 15, H/7, Olive Brown. Young under surface: Plate 56, J/10, Catawba.
*Rachis (the supporting stem of compound leaf).*—Medium. Upper side: smooth grooved. Under side: moderately smooth.
*Stipules.*—Moderately long; narrow width; with medium-long points; turning out at an angle of more than 45°; recurved toward the stem.
*Disease.*—Resistance comparable to the average variety growing under the same cultural conditions.

GROWTH

Habit: Bushy; upright; much branched.
Growth: Moderate vigor.
Canes: Medium.
Main stems:
*Color.*—Plate 23, L/3, Hellebore Green.
*Prickles.*—Several. Color: Plate 14, H/12, Bombay.
*Hairs.*—None.
Branches: Bright.
*Color.*—Plate 22, L/7, Art Green.
*Prickles.*—Few. Color: Plate 22, L/2, Palm Green.
*Hairs.*—None.
New shoots: bright.
*Color.*—Plate 14, L/6, Citrine-Rhubarb.
*Prickles.*—Many. Color: Plate 14, A/9, Pecan Brown.
*Hairs.*—None.

I claim:

1. A new and distinct variety of rose plant of the Hybrid Tea Class obtained as a seedling from a seed parent of the White Satin variety and an unnamed pollen parent U.S. Plant Pat. No. 2,603 characterized by its ability to yield large long lasting blooms on a continuous basis in a greenhouse, substantially as shown and described.

* * * * *

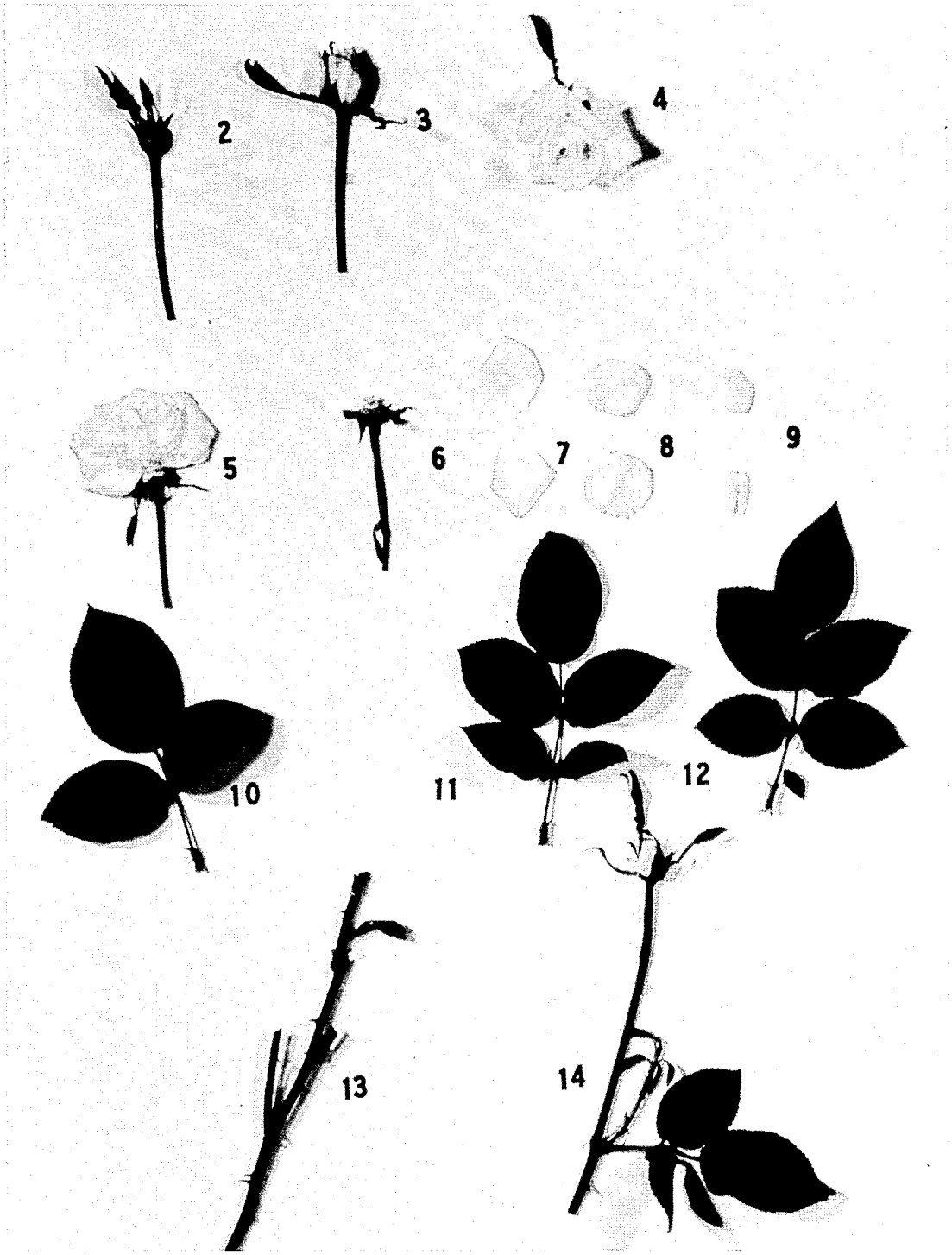
2
3
4
5
6
7
8
9
10
11
12
13
14